US00PP10724P

United States Patent [19]

Wain

[11] Patent Number: Plant 10,724

[45] Date of Patent: Dec. 15, 1998

[54] CHRYSANTHEMUM PLANT NAMED 'CREAM BI TIME'

[75] Inventor: Peter Wain, Portsmouth, United Kingdom

[73] Assignee: Cleangro, Ltd., West Sussex, United Kingdom

[21] Appl. No.: 838,349

[22] Filed: Apr. 8, 1997

[51] Int. Cl.[6] ..... A01H 5/00

[52] U.S. Cl. ..... Plt./82.2

[58] Field of Search ..... Plt./74.1, 82.1, Plt./82.2

*Primary Examiner*—Howard J. Locker
*Attorney, Agent, or Firm*—Christie, Parker & Hale, LLP

[57] ABSTRACT

A new variety of Chrysanthemum plant producing flowers with cream outer petals and a dark eye.

2 Drawing Sheets

BACKGROUND OF THE INVENTION

The present invention is directed to a new and distinct variety of chrysanthemum botanically classified as *Dendranthema grandiflora*. The varietal denomination of the new chrysanthemum is 'Cream Bi Time.'

'Cream Bi Time' was discovered as a natural mutation on a single branch of the parent plant in a controlled cultivated planting of the variety 'Bi Time,' U.S. Plant patent application Ser. No. 08/232,653 (now abandoned). The new variety has been asexually reproduced by vegetative cuttings in Ventura County, Calif. and the distinguishing characteristics are retained through successive generations of asexual reproduction.

SUMMARY OF THE INVENTION

'Cream Bi Time ' is a pot forcing a spray type chrysanthemum plant variety producing flowers with cream outer petals and a dark eye, and capable of being grown commercially in a greenhouse.

BRIEF DESCRIPTION OF ILLUSTRATIONS

The accompanying photographs show typical specimens of the new variety with colors being as nearly true as possible with illustrations of this type.

One illustration shows 'Cream Bi Time'grown as a pinched pot mum and

The other illustration is a close-up of the flowers.

DESCRIPTION OF THE PLANT

The following description of the new variety is of specimens grown in a greenhouse in Oxnard, Ventura County, Calif. in the month of October. 'Cream Bi Time' has not been observed under all possible environmental conditions. The phenotype may vary significantly with variations in the environment such as temperature, light intensity, day length and cultural conditions.

Plants of the new variety have been grown successfully under temperature conditions averaging about 65° F. at night and about 75° to 85° F. during the day under light conditions of about 5,000 to 6,000 foot candles. The plants respond well to use of growth retardant, such as one B9 treatment at about 2,000 ppm. To produce a commercial product the plants may be pinched once with the center bud removed. It has been observed that the shelf life of 'Cream Bi Time' is about 27 days with the response time of about 8 weeks.

Color values are taken from The Royal Horticultural Society Colour Chart (R.H.S.C.C.).

Plant

Habit: Very upright.
Height: About 23 cm.
Branching characteristics: Many small breaks.
Number of breaks from pinch: About 4.
Typical container size to be grown in: 4", 6", 8", 10".
Length of lateral branches: Average — about 14 cm.
Stem color: Near 143C.

Foliage

Leaf arrangement: Alternate.
Number of leaves per lateral branch:
*Average number of leaves per lateral branch.*—About 35, many small leaves.
(1) *Size.*—Length — Average about 4.6 cm. Width — Average about 2.9 cm.
(2) *Shape.*—Ovate.
(3) *Attachment.*—Petioled.
(4) *Apex.*—Obtuse with slightly serrated tip.
(5) *Base.*—Tapered.

| (6) Color: | Mature | Young |
|---|---|---|
| Top: | Near 137A | Near 137B |
| Bottom: | Near 137C | Near 138A |

Margin: Lobed with very slight serrations.
Aspect: Undulating.
Surface characteristics:
*Top.*—Puberulent.
*Bottom.*—Puberulent.
Venation: Net; with main veins prominent on underside of leaf. Coloration of veins is near 145B.
Petiole:
(1) *Length.*—Average about 1.4 cm.
(2) *Color.*—Near 145A.
(3) *Other characteristics.* — Very slightly winged.
Stipule: 2 per mature leaf, very variable shapes and sizes, 2 or 3 lobed to different degrees.

Flower

Inflorescence form: Cymose cluster.
Flower form: Anemone.
Flower shape: Flat.

Flower color (general): Cream outer petals with dark eye, near 178A.

Blooms: Average about 8 blooms per branch.

(1) *Diameter.*—Average about 5 cm.

(2) *Depth.*—About 0.8 cm.

Sepal:

(1) *Number.*—About 35, average 0.4 in length, concave-convex shape, margin is entire and membranous.

(2) *Color.*—Near 137B.

(3) *General appearance.*—Small, claw-shaped, edged by a clear membrane.

Peduncle:

(1) *Length.*—Average about 6.2 cm.

(2) *Habit.*—Upright, very slight curve.

(3) *Surface.*—Tomentose.

(4) *Color.*—Near 137D.

(5) *Strength.*—Weak.

Bud:

(1) *Shape.*—Flattened sphere.

(2) *Diameter.*—Average about 0.7 cm.

(3) *Color.*—Near 143C.

(4) *Height.*—Average about 0.35 cm.

Ray florets:

(1) *Number per flower.*—About 24.

(2) *Fused.*—No.

(3) *Texture.*—Matte.

(4) *Shape.*—Elliptic.

(5) *Apex.*—3-lobed.

(6) *Base.*—Tapered.

(7) *Margin.*—Entire.

(8) *Aspect.*—Recurved.

(9) *Length.*—Average about 2.3 cm.

(10) *Width.*—Average about 0.6 cm.

*Color — top side.*—Immature: Near 11C with streak 183D. Mature: Near 11C. Fading: Near 18C.

*Color — under side.*—Immature: Near 11C with near 59C stripe. Mature: Near 11C with near 64A strip. Fading: Near 18D with faint purple streak near 183D.

Disc florets:

(1) *Number per flower.*—Average about 180.

(2) *Texture.*—Glossy.

(3) *Shape.*—Tubular flared toward tip.

(4) *Margin.*—5-lobed, acute tip.

(5) *Length.*—Average about 1 cm.

(6) *Width.*—Average about 0.4 cm at widest point.

(7) *Fragrance.*—Medium strength, musky.

*Color.*—The coloration of tips of the disc florets and of the dark eye is near 178A. Inmature: Near 7D, tips near 59B. Mature: Near 11B with maroon tips near 178A. Fading: Near 11C, maroon tips near 178A.

Description of flower as it ages: Anemone deepens and eye less apparent as disc flowers separate.

Reproductive Organs

Ray Florets:

*Pistillate.*—(1) Pistil number: 1 per flower. (2) Receptacle shape: Domed. (3) Stigma shape: Forked, curling out slightly. (4) Stigma color: Near 12A. (5) Style length: About 0.45 cm. (6) Style color: Clear.

Disc florets: Staminate and pistillate.

*Pistillate.*—(1) Pistil number: 1 per flower. (2) Stigma shape: Forked, pointed out slightly, wide tips, near 9B. (3) Style length: About 0.4 cm, near 154D.

*Staminate.*—(1) Stamen number: About 5. (2) Anther length: About 0.1 cm. (3) Anther shape: Linear. (4) Pollen color: Near 13B. (5) Pollen quantity: Present, not abundant.

What is claimed is:

1. A new and distinct variety of Chrysanthemum plant substantially as herein shown and described.

* * * * *

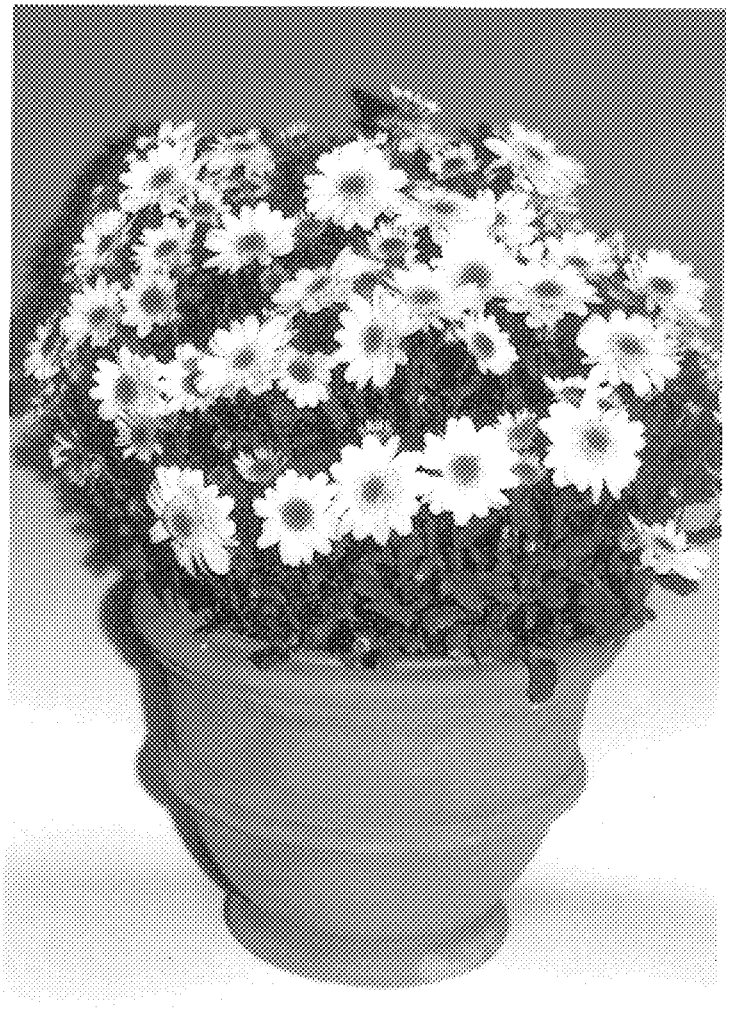

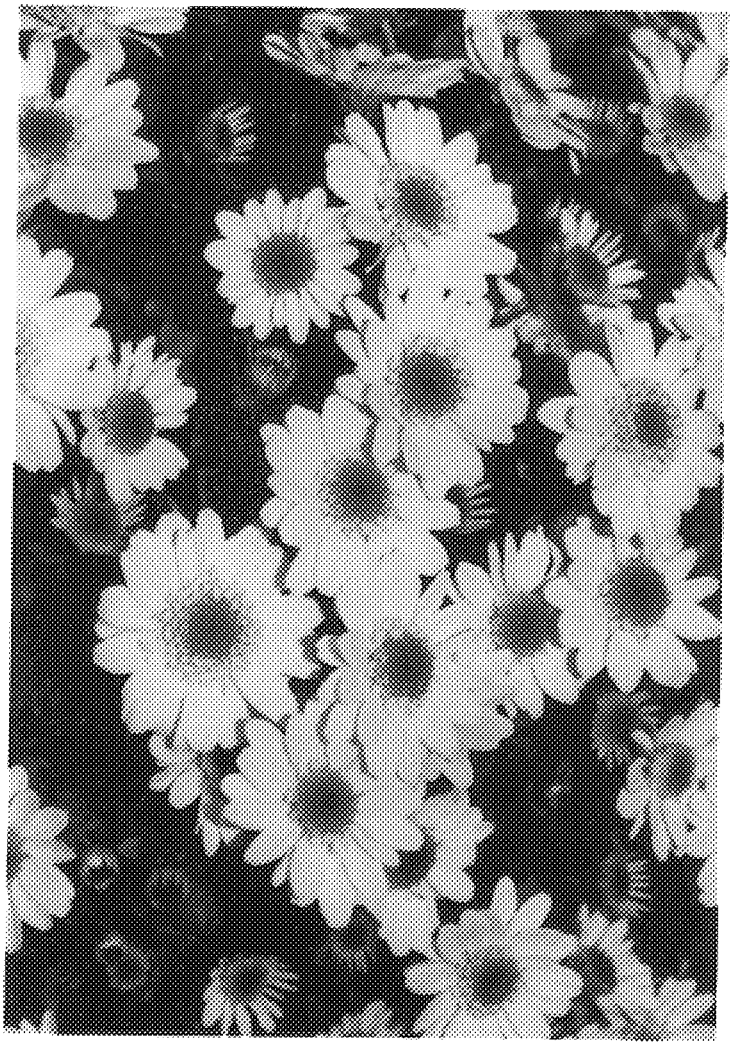

UNITED STATES PATENT AND TRADEMARK OFFICE

CERTIFICATE OF CORRECTION

PATENT NO. : Plant 10,724
DATED : December 15, 1998
INVENTOR(S) : Peter Wain

It is certified that error appears in the above-identified patent and that said Letters Patent is hereby corrected as shown below:

Column 3, line 7, after "0.4" insert -- cm --.
Column 4, line 2, change "64A strip" to -- 64A stripe --.

Signed and Sealed this

Eleventh Day of April, 2000

*Attest:*

*Attesting Officer*

Q. TODD DICKINSON

*Director of Patents and Trademarks*